United States Patent
Chen et al.

(10) Patent No.: US 7,619,423 B2
(45) Date of Patent: Nov. 17, 2009

(54) DIRECT METHOD AND APPARATUS FOR TESTING ANTICORROSION PERFORMANCE OF AQUEOUS PROTECTIVE FLUIDS WITH WIRE BEAM ELECTRODE SENSORS

(76) Inventors: Diping Chen, No. 326, South Lushan Road, Yuelu District, Changsha (CN) 410082; Hao Jin, No. 326, South Lushan Road, Yuelu District, Changsha (CN) 410082; Jiucheng Jin, No. 326, South Lushan Road, Yuelu District, Changsha (CN) 410082; Zhendao Wang, No. 326, South Lushan Road, Yuelu District, Changsha (CN) 410082; Guifang Huang, No. 326, South Lushan Road, Yuelu District, Changsha (CN) 410082; Xiaoli Zhu, No. 326, South Lushan Road, Yuelu District, Changsha (CN) 410082

( * ) Notice: Subject to any disclaimer, the term of this patent is extended or adjusted under 35 U.S.C. 154(b) by 125 days.

(21) Appl. No.: 11/568,456

(22) PCT Filed: Apr. 25, 2005

(86) PCT No.: PCT/CN2005/000562

§ 371 (c)(1),
(2), (4) Date: Oct. 29, 2006

(87) PCT Pub. No.: WO2005/106428

PCT Pub. Date: Nov. 10, 2005

(65) Prior Publication Data

US 2007/0209429 A1    Sep. 13, 2007

(30) Foreign Application Priority Data

Apr. 30, 2004  (CN) .................. 2004 1 0023162
Jun. 3, 2004    (CN) .................. 2004 2 0036066 U

(51) Int. Cl.
*G01R 35/00*   (2006.01)
*G01N 17/02*   (2006.01)
(52) U.S. Cl. ........................ 324/700; 73/104
(58) Field of Classification Search ............ 324/700, 324/115; 205/775.5, 776.5; 204/40; 73/104
See application file for complete search history.

(56) References Cited

U.S. PATENT DOCUMENTS

| | | | | |
|---|---|---|---|---|
| 1,811,765 A | * | 6/1931 | Snelling | 205/776.5 |
| 4,863,571 A | * | 9/1989 | Chambaere | 205/776.5 |
| 2005/0274628 A1 | * | 12/2005 | Yang | 205/775.5 |

* cited by examiner

*Primary Examiner*—Vincent Q Nguyen
(74) *Attorney, Agent, or Firm*—Matthias Scholl P.C.; Matthias Scholl

(57) ABSTRACT

A method for testing anticorrosion performance of an aqueous protective fluid by immersing a testing electrode comprising a plurality of individual electrodes insulated from and spaced with respect to one another into an aqueous protective fluid; immersing a reference electrode into the aqueous protective fluid at a predetermined distance from the testing electrode; connecting an Ohmmeter sequentially between each of the individual electrodes and the reference electrode to measure a plurality of electrical resistances between each of the individual electrodes and the reference electrode whereby obtaining a distribution of resistances. The distribution of resistances defines the anticorrosion performance of the aqueous protective fluid.

15 Claims, 2 Drawing Sheets

DIRECT METHOD AND APPARATUS FOR TESTING ANTICORROSION PERFORMANCE OF AQUEOUS PROTECTIVE FLUIDS WITH WIRE BEAM ELECTRODE SENSORS

CROSS-REFERENCE TO RELATED APPLICATIONS

This is a National Stage Application of International Patent Application No. PCT/CN 2005/000562 with an international filing date of Apr. 25, 2005, which is based on Chinese Patent Application No. 200410023162.3, filed Apr. 30, 2004 and on Chinese Patent Application No. 200420036066.8 filed Jun. 3, 2004. The contents of all these specifications are incorporated herein by reference.

BACKGROUND OF THE INVENTION

1. Field Of The Invention

This invention relates to a rapid high-resolution test method and apparatus for anticorrosion performance testing of aqueous protective fluids.

2. Background Of The Invention

Aqueous protective fluids contain oil preparations and emulsions of corrosion inhibitors dispersed in water. Organic protective oils feature good anticorrosion performance and easy removal, thus have a wide use. However, because they are water insoluble, organic protective oils cause considerable environmental pollution and are regulated by many industrialized countries. Aqueous protective fluids, on the other hand, cause few environmental pollution and, even though having relatively poor anticorrosion performance, they are widely used as lubricants for metal materials, as grinding fluids for temperature control during cold processing, and as corrosion protectors during manufacture and short-term storage of metal materials. As various countries become more and more environmentally conscious and intensify their efforts to monitor and protect the environment, aqueous protective fluids will gain popularity.

Currently, although many various types and brands of aqueous protective fluids are commercially available, the testing methods generally applied to evaluate anticorrosion performance include the ISO salt-spray method, humidity test, atmospheric corrosion rest, scrap iron test and laminated test. However, it is difficult to obtain accurate results using those methods for aqueous protective fluids and only qualitative result can be obtained. In addition, known testing methods require long testing times. Therefore, a rapid method for testing of anticorrosion performance of aqueous protective fluids having a high resolution, as well as a corresponding test apparatus for a more efficient testing is needed to satisfy the market demand and the scientific research of various countries. A method for testing the anticorrosion ability of protective oils with wire beam electrode, was recently described in "Research of anticorrosion performance of protective oil with wire beam electrode" *China Materials Protection*, 1996, 29(4): 9-10; "Influencing factors on the anticorrosion performance of protective oil and characteristics of metal corrosion under oil film" *Journal of Chinese Society for Corrosion and Protection*, 1999, 19(3): 179-184; and "Discussion on the partial corrosion of metals under oil film" *Corrosion science and Protection Technology*, 2000, 12(1): 30-31. This method employs a wire beam electrode sensor, which is first coated with protective oils and is then inserted into a corrosive solution of NaCl (5%) to test the anticorrosion performance of the oil. Even though this method can be performed easily and precisely, it is not suitable for aqueous protective fluids. This is because once a sensor is inserted into an water-based sodium chloride solution, aqueous protective fluids would most likely dissolve in the testing medium before its anticorrosion performance could be assessed.

DESCRIPTION OF THE INVENTION

In view of the above-described problems, it is one objective of the present invention to provide a direct, simple and efficient method having a high resolution for testing of anticorrosion performance of aqueous protective fluids using a wire beam electrode sensor.

It is another objective of the present invention to provide a testing apparatus with a wire beam electrode sensor having a simple structure and high precision that can fulfill the above function of testing the anticorrosion performance of aqueous protective fluids.

In accordance with one objective of the present invention, provided is a method for directly testing the anticorrosion performance of aqueous protective fluids with a wire beam electrode sensor, wherein N mini-electrodes insulated from each other comprise a working electrode whose working face works as a detecting sensor; the working electrode is partly submerged in aqueous protective fluids, the anticorrosion performance of which is to be tested; a power supply, said detecting sensor, aqueous protective fluids, and a reference electrode comprise a closed circuit for performing the resistance testing in a predetermined time interval so as to obtain the distribution of the resistances of the N mini-electrodes; only the working face of the working electrode is contacted with aqueous protective fluids; and the anticorrosion performance of the aqueous protective fluids at the working face of an $i^{th}$ electrode is evaluated by the resistance $R_i$, where the larger the resistance $R_i$, the stronger the anticorrosion ability.

The anticorrosion performance of aqueous protective fluids is evaluated by the distribution of resistances in the low resistance regions.

In one embodiments of the present invention, the resistance distribution range of the N pieces electrodes in low resistance regions is expressed by $n_i$, $n_2$, $n_3$, $n_4$, and $n_5$, where $n_1$ is the total number of electrodes of the N electrodes whose resistance values fall into the range of $\leq 10^3 \Omega$; $n_2$, $n_3$, $n_4$, and $n_5$ is the total number of electrodes of the N electrodes whose resistance values fall into the range of $10^4 \Omega$, $10^5 \Omega$, $10^6 \Omega$, and $10^7 \Omega$, respectively; $n_1$ corresponds to a poor anticorrosion ability of the fluid film in this region, so that the electrodes protected by this fluid film are easy corroded when exposed in a corrosive medium, and corrosion spots will appear quickly; $n_i$, $n_2$, $n_3$, $n_4$, and $n_5$ correspond to an increasing anticorrosion ability of the fluid film in their respective regions, and accordingly, corrosion spots will appear slowly compared with those in $n_1$ region; $n = n_1 + 0.9\ n_2 + 0.75\ n_3 + 0.5\ n_4 + 0.2\ n_5$, and is assumed to approximately express the equivalent number of corroded electrodes of the N electrodes under the action of a corrosive medium. The lower the n value, the stronger the anticorrosion ability of the aqueous protective fluids. Defined is also $$\overline{\log R} = \sum_{i=1}^{N} \log R_i / N$$

where $\overline{\log R}$ reflects an overall anticorrosion performance of aqueous protective fluids, and N is the total number of electrodes; a bigger $\overline{\log R}$ means a better anticorrosion performance under equivalent condition of n being the same.

Defined is also $$\sigma = \frac{\sqrt{\sum_{i=1}^{N}(\log R_i - \overline{\log R})^2}}{(N-1)}$$

where σ reflects the dispersion or nonuniformity of the anticorrosion performance of N fluid film regions, and N is the total number of working electrode; a smaller σ means a better anticorrosion performance under the condition for n being the same and $\overline{\log R}$ being the same.

In certain embodiments of the present invention, preferably, the working electrode, the reference electrode and the metal to be protected are made of identical metal material. When different aqueous protective fluids are to be tested, the working face of the working electrode is disposed at a fixed distance across from the plane of the reference electrode.

In certain embodiments of the present invention, the diameter of the metal wire comprising said working electrode is about 0.3-2.0 mm, and particularly about 0.7-0.9 mm.

In certain embodiments of the present invention, the working electrode comprises from 40 to 200 pieces, and particularly 64 pieces, of metal wires; and except for the working face of the metal wires, other portions to be submerged in aqueous protective fluids are encapsulated and sealed in an insulating resin at predetermined distance of from 1 to 5 mm apart from each other.

In certain embodiments of the present invention, the working electrode comprises 64 metal wires having an optimum diameter of from 0.7 to 0.9 mm disposed at predetermined distances of 2.5 mm apart from each other; and the reference electrode is made of steel plate. The plane of said working electrode is disposed at a constant distance of from 3 to 15 mm opposite to the plane of said reference electrode.

In certain embodiments of the present invention, the power supply supplies from 0.4 to 2 V of voltage.

In accordance with the principles of modern electrochemical theory, at room temperatures, the corrosion of metal under aqueous protective fluids is an electrochemical process, wherein the anticorrosion performance can be evaluated using polarization resistance. The measured resistance of an electrode is mainly comprised of the polarization resistance at the surface of the metal electrode and the resistance of the fluid film. The resistance of the fluid film can be used to evaluate the anticorrosion performance of the fluid film; the larger the resistance, the lower the corrosion speed of the metal, and thus the better the anticorrosion performance of aqueous protective fluids. $R_i$ reflects a protective ability in the fluid film region of an $i^{th}$ electrode. Generally, the resistance of each electrode is different. Experimental results show that the resistance falls into the range of about $10^2 \sim 10^{11} \Omega$. The area of fluid film can be divided into two regions, namely the I region and the D region, where I region has a large resistance, expressing a strong anticorrosion capability, and the D region has a small resistance. Liking to a weak link of a dam, the metal in this region will corrode firstly, so that the protective capability of the fluid film is bottlenecked in this region. The anticorrosion performance of different aqueous protective fluids can be compared according to the measured distribution of resistances.

Since no additional water or salt water is used during the testing process of the present invention, the dissolution of aqueous protective fluids in water is avoided. Moreover, the test can be performed in 10 to 20 minutes, which is 2 orders of magnitude faster than the ISO salt spray and the humidity test methods, and 3 orders of magnitude faster than the ISO atmospheric exposure method. In addition, the testing method of the present invention also provides quantitative results with high evaluating precision, and is little influenced by human factors. Accordingly, important economic and social benefits can be realized.

The conventional apparatus for resistance measurement as well as the apparatus in accordance with the present invention are suitable for use in the testing method of the present invention.

In accordance with another objective of the present invention, provided is an apparatus for testing the resistance efficiently and conveniently, comprising a working electrode; a reference electrode; a multiway switch; a sampling resistor; a reference voltage source; a program-controlled amplifier; an A/D converter; and an MCU controller, wherein the working electrode is connected with one end of the sampling resistor via the multiway switch and the reference voltage source; the other end of the sampling resistor is connected with the reference electrode; the input end of the program-controlled amplifier is connected with the sampling resistor in parallel, while the output end is connected to the input end of the A/D converter; the output end of the A/D converter is connected with the MCU controller; and the MCU controller is connected with the control port of the multiway switch.

In certain embodiments of the present invention, said reference voltage source supplies a voltage of from 0.4 to 2V.

In certain embodiments of the present invention, said working electrode comprises from 40 to 200 pieces of equally spaced metal wire whose portions to be submerged in aqueous protective fluids to be tested are encapsulated by an insulating resin except for the working face.

As a result, the present invention provides the apparatus of a rapid detector for testing of anticorrosion performance of aqueous protective fluids, with the advantages of simple structure, small size, easy portability, low price, short testing period, high measuring precision, and convenient and repeatable operation, wherein the time periods of production, development, application, as well as quality supervision and inspection of anticorrosion agents can be largely shortened.

1—working electrode; 2—epoxy resin; 3—reference electrode; aqueous protective fluids—4; working face of detecting sensor—5.

DETAILED DESCRIPTION OF THE EMBODIMENTS

Figures 2, 3:
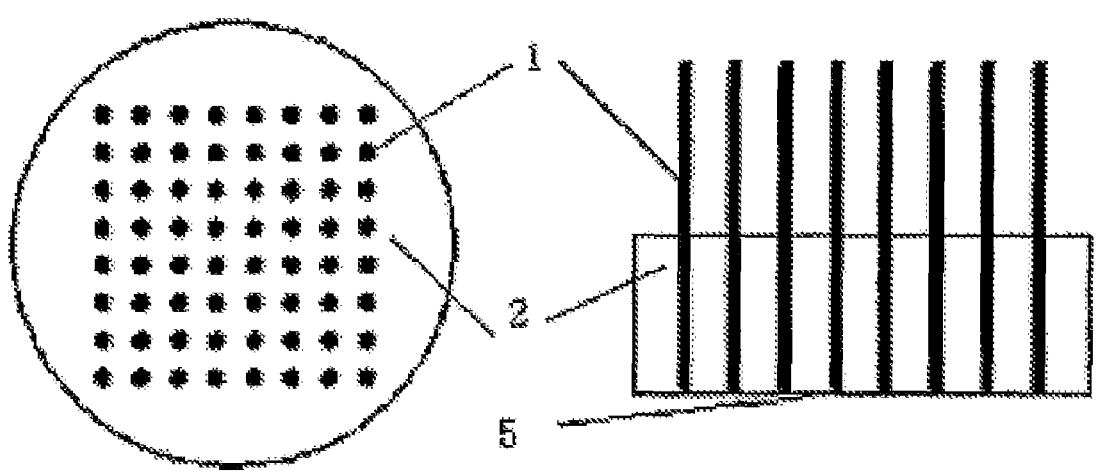
FIG. 2 is a front view of a detecting sensor in accordance with one embodiment of the present invention.
FIG. 3 is a side view of a detecting sensor in accordance with one embodiment of the present invention.

With reference to FIGS. 2-3, in accordance with one embodiment of the present invention, a working electrode 1 comprising 64 pieces of iron-based wire having an optimum diameter of 0.9 mm and being insulated from each other at an uniform interval of 2.5 mm is immersed, except the working face of the working electrode, in a sealing epoxy resin 2. Only the working face of the working electrode 5 is contacted with aqueous protective fluids 4 to be tested.

Figure 1:
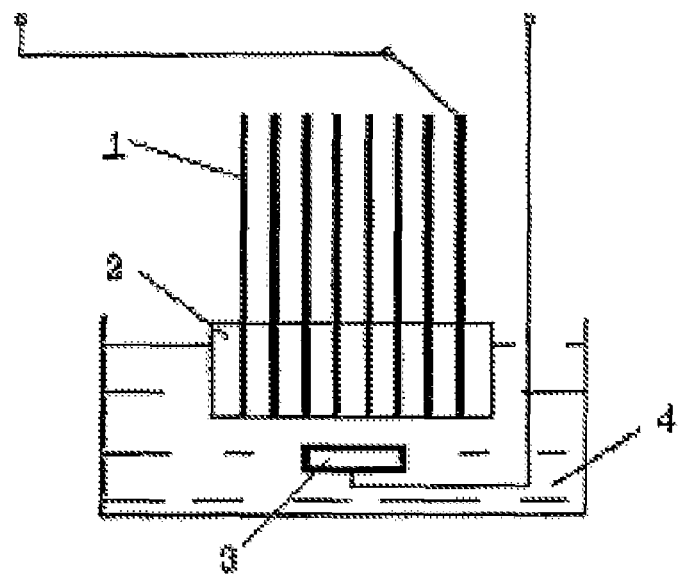
FIG. 1 illustrates a testing apparatus in accordance with one embodiment of the present invention.

As shown in FIG. 1, the working face 5 is immersed directly into aqueous protective fluids 4 after being orderly polished with emery paper of numbers 1-5 and being cleaned with petroleum ether or benzene, acetone and alcohol. The plane of a reference electrode 3 is disposed opposite to the plane of the detecting sensor at a predetermined distance of between 3 and 15 mm. A power source with the detecting sensor, aqueous protective fluids, and the reference electrode constitute a closed corrosive circuit so as to measure the resistance of the 64 electrodes to a voltage of 1IV provided by the power source under the conditions of room temperature 20-25° C., and ≦70% humidity. The resistance obtained from the measurement is the sum of the polarization resistance and the resistance of the solution, wherein the former constitutes a main portion, and accordingly the later constitutes a small portion.

Figure 4:
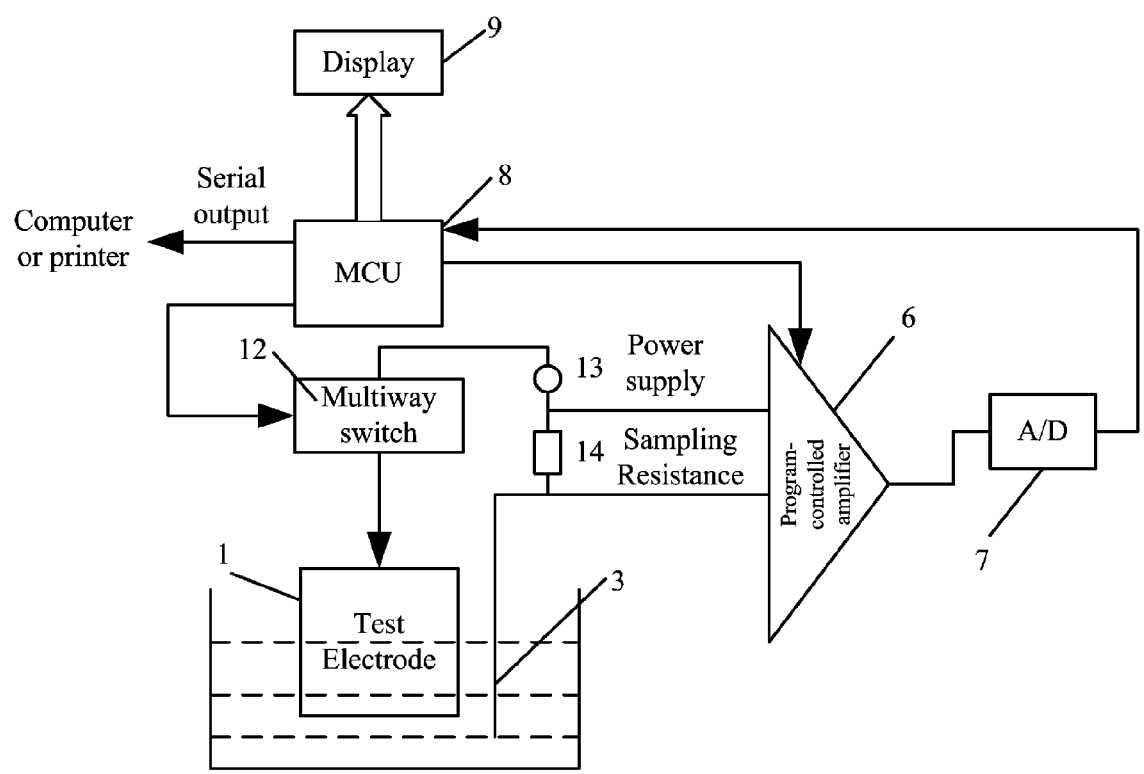
FIG. 4 is a circuit diagram of a test apparatus in accordance with one embodiment of the present invention.

With reference to FIG. 4, a test apparatus in accordance with the present invention comprises:

a working electrode 1; a reference electrode 3; a multiway switch 12; a reference voltage source 13; a sampling resistor 14; a program-controlled amplifier 6; an A/D converter 7; a MCU controller 8; and a display 9, wherein the working electrode 1 is connected to one end of the sampling resistor 14 via the reference voltage source 13 and the multiway switch 12, the other end of the sampling resistor 14 is connected with the reference electrode 3, the input end of the program-controlled amplifier 6 is connected with the sampling resistance in parallel; the output end of the program-controlled amplifier 6 is connected to the input end of the A/D converter 7; the output end of the A/D converter 7 is connected with the MCU controller; the output control ports of the MCU controller are connected with the multiway switch 12 and the control port of the program-controlled amplifier 6 respectively; the display 9 is connected with the MCU controller; and the serial port of the MCU controller is connected to a computer or a printer.

The electronic parts and components such as the multiway switch, the program-controlled amplifier, the A/D converter, the MCU controller, and the display in the testing apparatus are currently commercially and technologically available.

The working principle of the test apparatus in accordance with the present invention is described below: when testing protective samples, a working electrode 1 and a reference electrode 3 are dipped into the anticorrosion agent to constitute a closed circuit together with a multiway switch 12, a reference voltage source 13, and a sampling resistor 14 so as to carry out the resistance test. After the current/voltage passes through the sampling resistor, a resistance is measured and amplified by a program-controlled amplifier 6, and is then sent to an A/D converter 7 to be converted to a digital signal, and is then sent to a MCU controller 8 for processing; finally, the test results are stored and displayed. The multiway switch 12 controlled by the MCU controller 8 is used to orderly switch on and test the resistance of each metal wire of the working electrode 1 so as to obtain a resistance distribution of aqueous protective fluids. The resistance distribution of aqueous protective fluids, the average value of the logarithmic resistance, and the mean square error of resistance to the electrode are then calculated and analyzed and the anticorrosion performance of aqueous protective fluids is evaluated.

Under the conditions of constant distance between the working electrode and the reference electrode and constant voltage, the test results on aqueous protective fluids in accordance with the test method of the present invention are obtained and listed in Table 1; for comparison, the test results of salt spray and humidity test of 17 aqueous protective fluids are listed in Tables 2-4.

Samples of aqueous protective fluids were obtained as follows, 1#-4# were provided by the Wuhan Institute of Material Protection, China; 5#-11# were provided by the China National South Aeroengine Company; 12#-17# were provided by America ArvinMeritor Incorporation servicing American markets, in which: 1#—T870 (5% in $H_2O$); 2#—T870 (2% in $H_2O$ ); 3#—T870 (10% in $H_2O$ ); 4#—T839 (30% in xylene); 5#—Masida M206 (10); 6#—Masida M210 (10%); 7#—DX142 golden working fluid (10%); 8#—H-1 golden working fluid (10%); 9#—H-1 golden working fluid (5%); 10#—F-4A cleanser (5%); 11#—F-2 cleanser (5%); 12#—Irmco Fluids 116-Occ; 13#—P3 prevox 505; 14#—P3 prevox 510; 15#—R 1-5; 16#—SF (safe Film) 2838M; and 17#—Irmco Fluids 819-0cc.

TABLE 1

Test results of 17 aqueous protective fluids in accordance with the present invention.

| Sample No. | Test time (min) | Number of electrodes showing the various orders of resistance magnitude ($\Omega$) | | | | | | | | | n | $\overline{\log R}$ | $\sigma$ |
|---|---|---|---|---|---|---|---|---|---|---|---|---|---|
| | | $\leq 10^3$ | $10^4$ | $10^5$ | $10^6$ | $10^7$ | $10^8$ | $10^9$ | $10^{10}$ | $\geq 10^{11}$ | | | |
| 1 | 10~20 | 0 | 0 | 55 | 9 | 0 | 0 | 0 | 0 | 0 | 45.75 | 6.05 | 0.15 |
| 2 | | 0 | 0 | 57 | 7 | 0 | 0 | 0 | 0 | 0 | 46.25 | 6.02 | 0.01 |
| 3 | | 0 | 0 | 51 | 13 | 0 | 0 | 0 | 0 | 0 | 44.75 | 6.05 | 0.15 |
| 4 | | 0 | 0 | 0 | 0 | 3 | 60 | 0 | 1 | 0 | 0.6 | 8.54 | 0.23 |
| 5 | 10~20 | 0 | 0 | 9 | 55 | 0 | 0 | 0 | 0 | 0 | 34.3 | 6.10 | 0.022 |
| 6 | | 0 | 0 | 4 | 60 | 0 | 0 | 0 | 0 | 0 | 33.0 | 6.11 | 0.014 |
| 7 | | 0 | 0 | 0 | 64 | 0 | 0 | 0 | 0 | 0 | 32.0 | 6.13 | 0.014 |
| 8 | | 0 | 0 | 0 | 58 | 2 | 0 | 2 | 2 | 0 | 29.4 | 6.54 | 0.123 |
| 9 | | 0 | 0 | 21 | 43 | 0 | 0 | 0 | 0 | 0 | 37.3 | 6.12 | 0.030 |
| 10 | | 0 | 0 | 0 | 63 | 1 | 0 | 0 | 0 | 0 | 31.7 | 6.49 | 0.025 |
| 11 | | 0 | 0 | 55 | 9 | 0 | 0 | 0 | 0 | 0 | 45.8 | 5.78 | 0.023 |
| 12 | 10~20 | 0 | 1 | 30 | 9 | 2 | 0 | 0 | 22 | 0 | 27.3 | 7.23 | 1.97 |
| 13 | | 0 | 6 | 48 | 5 | 0 | 0 | 0 | 5 | 0 | 43.9 | 5.93 | 1.58 |
| 14 | | 0 | 6 | 44 | 5 | 0 | 0 | 0 | 9 | 0 | 40.9 | 6.30 | 1.60 |
| 15 | | 0 | 0 | 0 | 0 | 5 | 0 | 1 | 58 | 0 | 1.0 | 9.89 | 0.85 |
| 16 | | 0 | 0 | 0 | 0 | 0 | 0 | 61 | 3 | 0 | 0 | 9.33 | 0.15 |
| 17 | | 0 | 1 | 30 | 15 | 3 | 0 | 0 | 15 | 0 | 31.5 | 6.97 | 1.94 |

Comparing the n, $\overline{logR}$, and σ values of samples 1#-4#, the anticorrosion capability of the samples is 4#>3#>1#>2#. Comparing the n, $\overline{logR}$, and σ values of samples 5#-11#, the anticorrosion capability of the samples is 8#>10#>7#>6#>5#>9#>11#. Comparing the n, $\overline{logR}$, and σ values of samples 12#-17#, the anticorrosion capability of the samples is 16#>15#>12#>17#>14#>13#.

TABLE 2

Results of salt spray and humidity test tests of samples 1#-4# provided by the Wuhan Institute of Material Protection

| Sample No. | Salt spray 24 h | Wet heat 24 h | 72 h | 96 h | 720 h |
|---|---|---|---|---|---|
| 1 | rust, grade 3 | no rust, grade 0 | rust, grade 1 | / | / |
| 2 | / | no rust, grade 0 | rust, grade 1 | / | / |
| 3 | / | no rust, grade 0 | / | rust, grade 1 | / |
| 4 | rust, grade 2 | no rust, grade 0 | no rust, grade 0 | no rust, grade 0 | rust, grade 1 |

TABLE 3

Results of humidity test test on samples 5#-11# provided by China National South Aeroengine Company

| Sample No | 3 h | 8 h | 24 h | 48 h | 72 h | 96 h | 120 h | 144 h | 168 h |
|---|---|---|---|---|---|---|---|---|---|
| 5 | grade 0 | grade 0 | grade 0 | Grade 0 | grade 0 | grade 0 | grade 0 | grade 1 | |
| 6 | grade 0 | grade 0 | grade 0 | grade 0 | grade 0 | grade 0 | grade 0 | grade 0 | grade 1 |
| 7 | grade 0 | grade 0 | grade 0 | grade 0 | grade 0 | grade 0 | grade 0 | grade 0 | grade 1 |
| 8 | grade 0 | grade 0 | grade 0 | grade 0 | grade 0 | grade 0 | grade 0 | grade 0 | grade 0 |
| 9 | grade 0 | grade 0 | grade 0 | grade 0 | grade 0 | grade 0 | grade 1 | | |
| 10 | grade 0 | grade 0 | grade 0 | grade 0 | grade 0 | grade 0 | grade 0 | grade 0 | grade 1 |
| 11 | grade 0 | grade 0 | grade 0 | grade 0 | grade 0 | grade 1 | | | |

TABLE 4

Comparison of anticorrosion capabilities of samples 12#-17# (based on the results of salt spray and humidity test by America ArvinMeritor and many years of experience of the supplier; the anticorrosion capability is classified in three grades)

| | |
|---|---|
| 16# > 15# | Good |
| 12# > 17# | Bad |
| 14# > 13# | Worst |

Comparing the above data of 17 types of aqueous protective fluids, it is obvious that the results in accordance with the methods of the present invention are consistent with those tested by the ISO salt spray and humidity test, yet provide the advantages of short testing time, accurate quantification, and high resolution.

Appendix 1: Wuhan Institute of Material Protection samples 1#-4#, salt spray and humidity test report Appendix 2: China National South Aeroengine Testing Center samples 5#-11#, humidity test report Appendix 1

Wuhan Institute of Material Protection Testing Report

1. Samples of Aueous Potective Fluids:
T870 (5% in $H_2O$ ); T870 (2% in $H_2O$ ); T870 (10% in $H_2O$ ); T839 (30% in xylene)

2. Test Objective
Resistance to neutral humidity test and salt spray test.

3. Test Method
Sample preparation conforms to SH/T 0218-92 "Rust protective oils and greases: Preparation methods of test specimens".

Humidity test conforms to GB/T 2361-92 "Rust protective oils and greases: Test method of humidity test"

Neutral salt spray test conforms to SH/T 0081-91 "Rust protective oils and greases: Test method of salt spray", with the test conditions of:

Test solution: 5±1% NaCl
Test temperature: 35±1 C°
PH value: 6.5-7.2
Settlement of salt spray: 1.0~2.0M 1/h. 80 $cm^2$
Air pressure: 98±10 kpa
Spraying way: Continuous 4. Test Results
Test results are graded according to SH/T 0533-92 "Rust protective oils and greases: Determination of anticorrosion performance of test specimen"

|  | Oil sample | 24 h | 72 h | 96 h | 720 h |
|---|---|---|---|---|---|
| humidity test | T870 (5% in $H_2O$) | no rust, grade 0 | rust, grade 1 | | |
| | T870 (2% in $H_2O$) | no rust, grade 0 | rust, grade 1 | | |
| | T870 (10% in $H_2O$) | no rust, grade 0 | | rust, grade 1 | |
| | T839 (30% in xylene) | no rust, grade 0 | no rust, grade 0 | no rust, grade 0 | rust, grade 1 |

|  | Oil sample | 24 h | 72 h | 96 h | 720 h |
|---|---|---|---|---|---|
| Salt spray test | T870 (5% in $H_2O$) | rust, grade 3 | | | |
| | T870 (2% in $H_2O$) | | | | |
| | T870 (10% in $H_2O$) | | | | |
| | T839 (30% in xylene) | rust, grade 2 | | | |

Tested by: FuZiNan Checked by: ZhangSanPing
Apr. 5, 2004 Seal

Appendix 2

China National South Aeroengine Company Testing Report

1. Samples of Aqueous Protective Fluids:
M206(10%); M210(10%); DX142(100%); H-1(10%); H-1(5%); F4A(5%); F-2(5%)

2. Test Objective
Resistance tohumidity test.

3. Test Method
Sample preparation conforms to SH/T 0218-92 "Rust protective oils and greases: Preparation methods of test specimens", specimens were prepared on 45# steel plate.
Humidity test conforms to GB/T 2361-92 "Rust protective oils and greases: Test method ofhumidity test"

4. Test Results
Test results are graded according to SH/T 0533-92 "Rust protective oils and greases: Determination of anticorrosion performance of test specimen"

Tester: XuJianMin Proof reader: OuYangFei Checker: LuShenZhen
Dec. 8, 2004
Seal

The Invention claimed is:

1. A direct testing method of anticorrosion performance of an aqueous protective fluid comprising: immersing a plurality of N electrodes insulated from each other to form a testing electrode having a working face into an aqueous protective fluid, with a reference electrode being disposed at a predetermined space, and measuring electrical resistance $R_i$ sequentially at each of the N electrodes with respect to the reference electrode by using an Ohmmeter with a power source, wherein only the working face of the testing electrode is contacted with the aqueous protective fluid; and the anticorrosion performance of the aqueous protective fluid is determined by the distribution of resistances in low resistance regions; wherein the distribution of resistances in low resistance regions is expressed by $n_1$, $n_2$, $n_3$, $n_4$, and $n_5$; where $n_1$ is the total number of electrodes in N electrodes whose resistance values are in the range of $\leq 10^3 \Omega$; and wherein $n_2$, $n_3$, $n_4$ and $n_5$ is the total number of electrodes in N electrodes whose resistance values are in the order of $10^4 \Omega$, $10^5 \Omega$, $10^6 \Omega$ and $10^7 \Omega$ respectively; wherein $n = n1+0.9n2+0.75n3+0.5n4+0.2n5$ is assumed to express the equivalent number of corroded electrodes in N electrodes under the action of corrosive medium, and the lower the n value, the stronger the anticorrosion capability.

| Sample | Time (h) | | | | | | | | |
|---|---|---|---|---|---|---|---|---|---|
| No. | 3 | 8 | 24 | 48 | 72 | 96 | 120 | 144 | 168 |
| M206 (10%) | grade 0 | grade 0 | grade 0 | grade 0 | grade 0 | grade 0 | grade 0 | rust, grade 1 | / |
| M210 (10%) | grade 0 | grade 0 | grade 0 | grade 0 | grade 0 | grade 0 | grade 0 | grade 0 | rust, grade 1 |
| DX142 (10%) | grade 0 | grade 0 | grade 0 | grade 0 | grade 0 | grade 0 | grade 0 | grade 0 | rust, grade 1 |
| H-1 (10%) | grade 0 | grade 0 | grade 0 | grade 0 | grade 0 | grade 0 | grade 0 | grade 0 | grade 0 |
| H-1 (5%) | grade 0 | grade 0 | grade 0 | grade 0 | grade 0 | grade 0 | rust, grade 1 | / | / |
| F4A (5%) | grade 0 | grade 0 | grade 0 | grade 0 | grade 0 | grade 0 | grade 0 | grade 0 | rust, grade 1 |
| F-2 (5%) | grade 0 | grade 0 | grade 0 | grade 0 | grade 0 | rust, grade 1 | / | / | / |

2. The method of claim 1, wherein $$\overline{\log R} = \sum_{i=1}^{N} \log R_i / N$$

indicates an overall anticorrosion performance of the aqueous protective fluid;
  N is the number of the electrodes; and
  a larger value of $\overline{\log R}$ indicates a better anticorrosion performance under the condition that the numbers of electrodes n in different resistance regions remains equal.

3. The method of claim 2, wherein $$\sigma = \sqrt{\frac{\sum_{i=1}^{N}(\log R_i - \overline{\log R})^2}{(N-1)}}$$

indicates the dispersion or nonuniformity of the anticorrosion performance of N fluid film regions;
  N is the number of electrodes; and
  a smaller σ means a better anticorrosion performance under the conditions that the values of n and $\overline{\log R}$ in different resistance regions remain equal.

4. The method of claim 1, wherein said testing electrode, said reference electrode and a metal to be protected are preferably made of identical metal material; when different aqueous protective fluids are tested, the plane of the testing electrode is disposed opposite to the plane of the reference electrode at a distance of from 3 to 15 mm.

5. The method of claim 4, wherein said testing electrode comprises from 40 to 200 metal wires; and except for the working face of the metal wires, other portions thereof to be submerged in aqueous protective fluids are sealed in an insulating resin at a distance of from 1 to 5 mm apart from each other.

6. The method of claim 4, wherein said power source supplies from 0.4 to 4 V of voltage.

7. The method of claim 1, wherein the diameter of the metal wire of the testing electrode is from 0.3 to 2 mm.

8. The method of claim 7, wherein said working electrode comprises from 40 to 200 metal wires; and except for the working face of the metal wires, other portions thereof to be submerged in aqueous protective fluids are sealed in an insulating resin at a distance of from 1 to 5 mm apart from each other.

9. The method of claim 1, wherein said testing electrode comprises from 40 to 200 metal wires; and except for the working face of the metal wires, other port ions thereof to be submerged in aqueous protective fluids are sealed in an insulating resin at a distance of from 1 to 5 mm apart from each other.

10. The method of claim 9, wherein said testing electrode comprises 64 pieces of metal wire.

11. The method of claim 9, wherein said testing electrode comprises 64 pieces of metal wires having an optimum diameter of from 0.7 to 0.9 mm disposed at a distance of 2.5 mm apart from each other; said reference electrode is made of steel plate; and said testing electrode is disposed at a distance of from 3 to 15 mm away from said reference electrode.

12. The method of claim 1, wherein said power source supplies from 0.4 to 4 V of voltage.

13. The method of claim 1, wherein measuring electrical resistance $R_i$ comprises forming a closed electrical circuit comprising the Ohmmeter, an $i^{th}$ electrode, the reference electrode and the aqueous protective fluid, wherein one terminal of the Ohmmeter is connected to the $i^{th}$ electrode, another terminal of the Ohmmeter is connected to the reference electrode, and the $i^{th}$ electrode and the reference electrode are contacted with the aqueous protective fluid.

14. The method of claim 1, wherein the anticorrosion performance of a fluid film at the working face region of an $i^{th}$ electrode is characterized by the resistance $R_i$, where the larger the $R_i$, the stronger the anticorrosion capability.

15. A method for testing anticorrosion performance of an aqueous protective fluid, comprising: immersing a testing electrode comprising a plurality of individual electrodes insulated from and spaced with respect to one another into an aqueous protective fluid; immersing a reference electrode into the aqueous protective fluid at a predetermined distance from the testing electrode; connecting an Ohmmeter sequentially between each of the individual electrodes and the reference electrode to measure a plurality of electrical resistances between each of the individual electrodes and the reference electrode whereby obtaining a distribution of resistances, wherein the distribution of resistances defines the anticorrosion performance of the aqueous protective fluid; wherein the resistances measured are grouped by their order of magnitude in Ω; wherein the distribution of resistances between 0 and $10^7 \Omega$ defines the anticorrosion performance of the aqueous protective fluid whereby the lower the count of resistances between 0 and $10^7 \Omega$ the better the anticorrosion performance of the aqueous protective fluid.

* * * * *

UNITED STATES PATENT AND TRADEMARK OFFICE
CERTIFICATE OF CORRECTION

| | |
|---|---|
| PATENT NO. | : 7,619,423 B2 |
| APPLICATION NO. | : 11/568456 |
| DATED | : November 17, 2009 |
| INVENTOR(S) | : Chen et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 143 days.

Signed and Sealed this

Fourteenth Day of December, 2010

David J. Kappos
*Director of the United States Patent and Trademark Office*